United States Patent
Khoshdel et al.

(10) Patent No.: US 10,034,824 B2
(45) Date of Patent: Jul. 31, 2018

(54) HAIR SHAPING COMPOSITION

(71) Applicant: Conopco, Inc., Englewood Cliffs, NJ (US)

(72) Inventors: Ezat Khoshdel, Neston (GB); Prem Kumar Cheyalazhagan Paul, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/523,150

(22) PCT Filed: Nov. 2, 2015

(86) PCT No.: PCT/EP2015/075448
§ 371 (c)(1),
(2) Date: Apr. 28, 2017

(87) PCT Pub. No.: WO2016/074969
PCT Pub. Date: May 19, 2016

(65) Prior Publication Data
US 2017/0333329 A1    Nov. 23, 2017

(30) Foreign Application Priority Data
Nov. 13, 2014 (EP) ..................... 14193096

(51) Int. Cl.
*A61K 8/60* (2006.01)
*A61Q 5/06* (2006.01)

(52) U.S. Cl.
CPC . *A61K 8/60* (2013.01); *A61Q 5/06* (2013.01)

(58) Field of Classification Search
CPC .................... A61K 8/60; A61Q 5/06
See application file for complete search history.

(56) References Cited

U.S. PATENT DOCUMENTS

| 4,542,014 A | 9/1985 | Bresak et al. |
| 2004/0166126 A1 | 8/2004 | Cannell et al. |
| 2006/0084656 A1* | 4/2006 | Ziegler ............... A61K 9/0043 514/249 |

FOREIGN PATENT DOCUMENTS

| EP | 0507272 | 6/1992 |
| WO | WO02078649 | 10/2002 |
| WO | WO02078655 | 10/2002 |
| WO | WO2009053163 | 4/2009 |
| WO | WO2013076061 | 5/2013 |

OTHER PUBLICATIONS

Hair & Scalp Stimulating Program, Mintel GNPD, 2011, pp. 1-5 (also cited as XP002738650).
Scalp Revitalizer, Database GNPD online Mintel 2012, 2012, pp. 1-4 (also cited as XP002738651).
Search Report in EP14193096, dated Apr. 20, 2015.
Search Report in EP14193097, dated Apr. 20, 2015.
Search Report in PCTEP2015075439, dated Dec. 8, 2015.
Search Report in PCTEP2015075448, dated Dec. 8, 2015.
Written Opinion in EP14193096, dated Apr. 20, 2015.
Written Opinion in EP14193097, dated Apr. 20, 2015.
Written Opinion in PCTEP2015075439, dated Dec. 8, 2015.
Written Opinion in PCTEP2015075448, dated Dec. 8, 2015.
Co-Pending Application, Ezat Khoshdel et al., filed Apr. 28, 2017.

* cited by examiner

*Primary Examiner* — Aradhana Sasan
(74) *Attorney, Agent, or Firm* — Karen E. Klumas

(57) ABSTRACT

The invention provides a hair shaping composition suitable for topical application to hair, the composition comprising from 1 to 25 wt % monoglucosamine adipate, dissolved or dispersed in an aqueous carrier. The invention also provides a method for improving hair volume-down which comprises the following steps: (i) treating the hair by topical application of the hair shaping composition as defined above; (ii) shaping the treated hair; (iii) allowing the composition to remain in contact with the shaped hair before drying. Advantageously the method of the invention does not require the breakage of the hair disulfide bonds, does not require the use of high temperature heated implements such as straightening irons, and can be accomplished by a consumer without intervention of a professional hairdresser.

6 Claims, No Drawings

HAIR SHAPING COMPOSITION

FIELD OF THE INVENTION

This invention relates to a hair shaping composition, and more particularly a hair shaping composition which does not require the breakage of hair disulfide bonds.

BACKGROUND AND PRIOR ART

"Frizzy" hair is a major hair care problem for some consumers, particularly those with coarse, wavy or curly hair. It is characterized by a multiplicity of fly-away strands and by excessive hair volume, which is the visible bulkiness of hair. Hair affected in this way tends to lose its natural shape and/or its curl definition. For consumers who desire well aligned and manageable hair, this is not desirable. The problem can worsen if the hair becomes dry or damaged for any reason.

A variety of approaches have been developed to reduce excessive volume and frizz. These include application of oily or resinous leave-on products to coat and weigh down the hair. However, usage of these products in large amounts commonly results in a poor perception of hair cleanliness. It may also leave the hair and hands with a tacky, dirty, feeling.

Other techniques used to control volume and frizz include reactive chemistry approaches aimed at a permanent restructuring of hair, and the use of high temperature heated implements such as straightening irons. However, all of these processes can cause a degree of mechanical or chemical damage to the hair if used excessively.

It is an object of the present invention to provide a hair shaping composition which provides improved hair volume-down benefits and/or curl definition, without the negatives associated with the prior art methods described above.

Another object of the present invention is to provide a method of shaping hair which does not require the breakage of the hair disulfide bonds, does not require the use of high temperature heated implements such as straightening irons, and can be accomplished by a consumer without intervention of a professional hairdresser.

SUMMARY OF THE INVENTION

The invention provides a hair shaping composition suitable for topical application to hair, the composition comprising from 1 to 25 wt % monoglucosamine adipate, dissolved or dispersed in an aqueous carrier.

The invention also provides a method for improving hair volume-down and/or curl definition, which comprises the following steps:
  (i) treating the hair by topical application of a composition as defined above;
  (ii) shaping the treated hair;
  (iii) allowing the composition to remain in contact with the shaped hair before drying.

DETAILED DESCRIPTION AND PREFERRED EMBODIMENTS

Glucosamine is 2-amino-2-deoxy-D-glucose, and is found in chitin, glycoproteins and glycosaminoglycans.

Monoglucosamine adipate is a salt which may be represented by the following general formula:

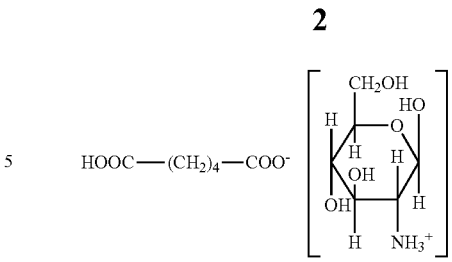

Monoglucosamine adipate may typically be prepared by obtaining the glucosamine base from glucosamine hydrochloride, and subsequently adding adipic acid.

Glucosamine base is generally obtained by treating glucosamine hydrochloride with triethylamine, or with sodium methoxide, or alternatively by means of anionic exchange resins. Monoglucosamine adipate may also be directly obtained from glucosamine hydrochloride, using an anionic exchange resin previously conditioned with adipic acid. Since adipic acid contains more than one carboxyl group, then the monoglucosamine salt may be obtained by appropriate choice of the starting quantity of glucosamine or glucosamine hydrochloride.

Preferably the level of monoglucosamine adipate ranges from 1 to 5 wt % and more preferably from 1 to 3 wt %, by weight based on the total weight of the composition.

Advantageously, the hair shaping composition of the invention does not require the incorporation of reducing agents, and a hair shaping composition according to the invention is generally substantially free of such materials. The term "substantially free" in the context of this invention means that reducing agents are absent or included in trace quantities only, such as no more than 0.1 wt %, preferably no more than 0.01 wt %, and more preferably from 0 to 0.001 wt % (by weight based on the total weight of the composition).

The term "reducing agent" in the context of this invention means an agent which is effective to break hair disulfide bonds when applied to hair for a period ranging from about 3 to 15 minutes and at a temperature ranging from about 20 to 30° C. Examples of such reducing agents are ammonium thioglycolate (in a solution having a pH of between about 7 and 10.5), glyceryl monothioglycolate (employed at a pH of less than 7), thioglycolic acid, dithioglycolic acid, mercaptoethyl amine, mercaptopropionic acid, dithioglycolate and alkali metal or ammonium sulfites or bisulfites.

A hair shaping composition according to the invention will generally comprise at least 60 wt %, preferably at least 70 wt % and more preferably at least 80 wt % water (by weight based on the total weight of composition). Preferably, the composition comprises no more than 99 wt % and more preferably no more than 98 wt % water (by weight based on the total weight of the composition). Other organic solvents may also be present, such as lower alkyl alcohols and polyhydric alcohols. Examples of lower alkyl alcohols include $C_1$ to $C_6$ monohydric alcohols such as ethanol and isopropanol. Examples of polyhydric alcohols include propylene glycol, hexylene glycol, glycerin, and propanediol. Mixtures of any of the above described organic solvents may also be used.

A hair shaping composition according to the invention may suitably have a conditioning gel phase, which may be generally characterized as a gel (Lβ) surfactant mesophase consisting of surfactant bilayers. Such a conditioning gel phase may be formed from a cationic surfactant, a high melting point fatty alcohol and an aqueous carrier. Typically these components are heated to form a mixture, which is cooled under shear to room temperature. The mixture undergoes a number of phase transitions during cooling, normally resulting in a gel (Lβ) surfactant mesophase consisting of surfactant bilayers.

Examples of suitable cationic surfactants which are useful for forming the conditioning gel phase include quaternary ammonium cationic surfactants corresponding to the following general formula:

$$[N(R^1)(R^2)(R^3)(R^4)]^+(X)^-$$

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halide, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Specific examples of such quaternary ammonium cationic surfactants of the above general formula are cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by other halide (e.g., bromide), acetate, citrate, lactate, glycolate, phosphate nitrate, sulphate, or alkylsulphate.

In a preferred class of cationic surfactant of the above general formula, $R^1$ is a $C_{16}$ to $C_{22}$ saturated or unsaturated, preferably saturated, alkyl chain and $R^2$, $R^3$ and $R^4$ are each independently selected from $CH_3$ and $CH_2CH_2OH$, preferably $CH_3$.

Specific examples of such preferred quaternary ammonium cationic surfactants for use in forming the conditioning gel phase are cetyltrimethylammonium chloride (CTAC), behenyltrimethylammonium chloride (BTAC) and mixtures thereof.

Mixtures of any of the above-described cationic surfactants may also be suitable.

The level of cationic surfactant suitably ranges from 0.1 to 10 wt %, preferably from 0.2 to 5 wt % and more preferably from 0.25 to 4 wt % (by total weight of cationic surfactant based on the total weight of the composition).

By "high melting point" in the context of this invention is generally meant a melting point of 25° C. or higher. Generally the melting point ranges from 25° C. up to 90° C., preferably from 40° C. up to 70° C. and more preferably from 50° C. up to about 65° C.

The high melting point fatty alcohol can be used as a single compound or as a blend or mixture of at least two high melting point fatty alcohols. When a blend or mixture of fatty alcohols is used, the melting point means the melting point of the blend or mixture.

Suitable fatty alcohols of this type have the general formula R—OH, where R is an aliphatic carbon chain.

Preferably R is a saturated aliphatic carbon chain comprising from 8 to 30 carbon atoms, more preferably from 14 to 30 carbon atoms and most preferably from 16 to 22 carbon atoms.

R can contain, in addition to carbon and hydrogen atoms, ether linkages, and other groups such as amino groups.

Most preferably, the fatty alcohol has the general formula $CH_3(CH_2)_n$ OH, where n is an integer from 7 to 29, preferably from 15 to 21.

Specific examples of suitable fatty alcohols are cetyl alcohol, stearyl alcohol, behenyl alcohol, and mixtures thereof. Cetyl alcohol, stearyl alcohol and mixtures thereof are particularly preferred.

Mixtures of any of the above-described fatty alcohols may also be suitable.

The level of fatty alcohol suitably ranges from 0.01 to 10 wt %, preferably from 0.1 to 8 wt %, more preferably from 0.2 to 7 wt % and most preferably from 0.3 to 6 wt % (by weight based on the total weight of the composition).

The weight ratio of cationic surfactant to fatty alcohol is suitably from 1:1 to 1:10, preferably from 1:1.5 to 1:8, optimally from 1:2 to 1:5.

A hair shaping composition according to the invention may also incorporate other optional ingredients to enhance performance and/or consumer acceptability. Suitable optional ingredients include: preservatives, colouring agents, chelating agents, antioxidants, fragrances, antimicrobials, antidandruff agents, cationic conditioning polymers, styling ingredients, sunscreens, proteins and hydrolysed proteins.

Preferably, the hair shaping composition is a single dose composition. The term "single dose" in the context of this invention means that the composition is to be topically applied to the hair in one go.

The hair shaping composition of the invention is suitable for topical application to hair for improved hair volume-down. The term "volume-down" in the context of this invention generally means reduced visible bulkiness of the hair. For many consumers, improved hair volume-down provides a number of associated benefits, such as improved manageability and improved style retention.

The hair shaping composition of the invention is also suitable for topical application to hair for improved curl definition.

The hair shaping composition of the invention is preferably topically applied to the hair at a temperature from 15 to 40° C., and more preferably at a temperature from 20 to 30° C.

Preferably, the composition is applied to dry hair. The term "dry hair" in the context of this invention generally means hair from which free water (i.e. water disposed as a film or droplets on the cuticle surface) has been substantially removed. Hair may be dried by exposure to air, by use of a heated hair drying appliance, by rubbing with a water-absorbent article, or by a combination of any of these methods. Preferably, the dry hair will not have been washed or actively wetted, (such as by shampooing, conditioning, rinsing or otherwise treating with an aqueous composition) in the preceding 2 hours and more preferably in the preceding 3 hours prior to topical application of the composition, and will have been permitted to acclimatise to atmospheric conditions. In such circumstances there is substantially no free water present which interferes with the adsorption of the composition on application. A suitable indicator of dry hair in the context of this invention would be a hair fibre whose calculated water content does not exceed 25 wt % by weight based on the total weight of the hair fibre.

In step (ii) of the method of the invention, the treated hair is shaped.

Shaping of the hair in the method of the invention can be accomplished by such means as the finger tips, a plastic hair pick or the tail of a comb, the shaping being performed on portions of the hair comprising strands of hair in various numbers. Using such means the hair may be pulled, combed, smoothed, pressed or flattened into a straightened configuration; or shaped gently into bends, waves or curls.

A hot tool, such as a flat hair iron or hand-held hair dryer, may be used in the hair shaping step. Such tools apply high levels of heat directly to the hair. Most operate in the 45° C. to 250° C. range, and are usually employed at temperature settings ranging from 50° C. to about 220° C., depending on the particular tool.

However, the use of hot tools is not essential in the method of the invention. This is especially advantageous for consumers who wish to reduce or avoid the exposure of their hair to high temperatures, for example if their hair is fragile or overprocessed from previous chemical treatments such as bleaching and perming.

Accordingly the shaping of the hair in step (ii) of the method of the invention is preferably conducted at a temperature from 15 to 60° C., more preferably at a temperature from 20 to 40° C.

Most preferably in step (ii) of the method of the invention the hair is shaped by combing it into a straightened configuration at a temperature from 20 to 40° C.

In step (iii) of the method of the invention, the composition is allowed to remain in contact with the shaped hair before drying.

Preferably the composition is allowed to remain in contact with the shaped hair until the hair is dry.

The hair may be dried naturally by exposure to air, by use of a heated hair drying appliance, by rubbing with a water-absorbent article, or by a combination of any of these methods.

The composition may thus remain in contact with the shaped hair for a period of at least about 3 minutes up to 3 hours or more if the hair is allowed to dry naturally.

The dried hair may be re-shaped if desired, such as by combing it into a straightened configuration at a temperature from 20 to 40° C.

The composition may then be rinsed from the hair at the next wash.

The invention is further illustrated with reference to the following, non-limiting Example.

All ingredients are expressed by weight percent of the total formulation, and as level of active ingredient.

Example

All ingredients are expressed by weight percent of the total formulation, and as level of active ingredient.

Dark brown European wavy#6 switches of length 25 cm and weight 2 gms (from the same batch of switches), were dosed with 0.2 ml of a 2% solution of monoglucosamine adipate. Control switches were treated with water.

All switches were combed straight and left to dry overnight.

When dry the switches were combed straight and pictures taken. The volume of the switches shows the volume-down benefit of the treatment (here volume refers to the projection of the switch image on to the screen and is given in $mm^2$). The percentage benefit (i.e. decrease in volume) with respect to control (water) is also given.

The results are shown in Table 1.

TABLE 1

| Treatment | Volume $mm^2$ | % benefit |
|---|---|---|
| Water (control) | 14182 | 0.0 |
| monoglucosamine adipate | 13047 | 8.0 |

The results show that treatment with monoglucosamine adipate according to the invention gives a significant hair volume-down benefit.

The treatment also provided excellent curl definition benefit.

The invention claimed is:

1. A hair shaping composition suitable for topical application to hair, the composition comprising from 1 to 25 wt % monoglucosamine adipate, dissolved or dispersed in an aqueous carrier.

2. The composition according to claim 1, in which the level of monoglucosamine adipate ranges from 1 to 5 wt %, by weight based on the total weight of the composition.

3. The composition according to claim 1, in which the level of reducing agents ranges from 0 to 0.001 wt % (by weight based on the total weight of the composition).

4. A method for improving hair volume-down and/or curl definition which comprises the following steps:
    (i) treating the hair by topical application of a composition according to claim 1;
    (ii) shaping the treated hair;
    (iii) allowing the composition to remain in contact with the shaped hair before drying.

5. The method according to claim 4, in which the hair is shaped in step (ii) by combing it into a straightened configuration at a temperature from 20 to 40° C.

6. The method according to claim 4, in which the composition is allowed to remain in contact with the shaped hair in step (iii) until the hair is dry.

* * * * *